(12) United States Patent
Zhang et al.

(10) Patent No.: US 11,833,264 B2
(45) Date of Patent: Dec. 5, 2023

(54) DEVICE COLD PLASMA STERILIZATION

(71) Applicants: Nanjing Agricultural University, Nanjing (CN); Suzhou Yirun Food Technology Co., Ltd., Suzhou (CN)

(72) Inventors: Jianhao Zhang, Nanjing (CN); Jiamei Wang, Suzhou (CN); Lianghao Wan, Suzhou (CN); Long Xu, Suzhou (CN)

(73) Assignees: NANJING AGRICULTURAL UNIVERSITY, Nanjing (CN); SUZHOU YIRUN FOOD TECHNOLOGY CO., LTD., Suzhou (CN)

( * ) Notice: Subject to any disclaimer, the term of this patent is extended or adjusted under 35 U.S.C. 154(b) by 534 days.

(21) Appl. No.: 17/133,586

(22) Filed: Dec. 23, 2020

(65) Prior Publication Data
US 2021/0113726 A1 Apr. 22, 2021

Related U.S. Application Data

(63) Continuation-in-part of application No. PCT/CN2018/119978, filed on Dec. 10, 2018.

(30) Foreign Application Priority Data

Nov. 8, 2018 (CN) .......................... 201811325297.3
Nov. 8, 2018 (CN) .......................... 201811325301.6
Nov. 8, 2018 (CN) .......................... 201811325923.9

(51) Int. Cl.
*A61L 2/14* (2006.01)
*A23L 3/00* (2006.01)

(52) U.S. Cl.
CPC ............. *A61L 2/14* (2013.01); *A61L 2202/11* (2013.01); *A61L 2202/14* (2013.01)

(58) Field of Classification Search
CPC ........... A61L 2/14; A61L 2202/14; A23L 3/00
See application file for complete search history.

(56) References Cited

U.S. PATENT DOCUMENTS

2005/0127843 A1* 6/2005 Koulik .................... B65B 55/10
 315/111.21

* cited by examiner

*Primary Examiner* — Kevin Joyner
(74) *Attorney, Agent, or Firm* — MATTHIAS SCHOLL P.C.; Matthias Scholl

(57) ABSTRACT

A device cold plasma sterilization includes a housing, a base, a conveying assembly, a plurality of core modules, a transformer, a control cabinet, a distribution box, a shielding door, and a controller. The housing is disposed on the base. The plurality of core modules is disposed in the housing along a moving direction of the conveying assembly and are spaced apart from each other. The plurality of core modules each include a plurality of electrode assemblies spaced from one another by equal distance and arranged in a row. The transformer, the control cabinet, and the distribution box are disposed in a lower part of the base and are connected to the plurality of electrode assemblies. The conveying assembly is disposed in a middle part of the base. The base includes an inlet for entry and an outlet for exit of a package to be sterilized.

12 Claims, 6 Drawing Sheets

DEVICE COLD PLASMA STERILIZATION

CROSS-REFERENCE TO RELATED APPLICATIONS

This application is a continuation-in-part of International Patent Application No. PCT/CN2018/119978 with an international filing date of Dec. 10, 2018, designating the United States, now pending, and further claims foreign priority benefits to Chinese Patent Application No. 201811325297.3 filed on Nov. 8, 2018, to Chinese Patent Application No. 201811325301.6 filed on Nov. 8, 2018, and to Chinese Patent Application No. 201811325923.9 filed on Nov. 8, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to a device cold plasma sterilization.

Conventionally, the sterilization of food is carried out at high temperatures. For heat sensitive food such as fresh fish and meat products and fresh fruits and vegetables, high temperature sterilization makes them lose original nutrition and taste.

SUMMARY

The disclosure provides a device cold plasma sterilization comprising a housing, a base, a conveying assembly, a plurality of core modules, a transformer, a control cabinet, a distribution box, a shielding door, and a controller. The housing is disposed on the base; the plurality of core modules is disposed in the housing along a moving direction of the conveying assembly and are spaced apart from each other; each of the plurality of core modules comprises a plurality of electrode assemblies spaced from one another by equal distance and arranged in a row; the transformer, the control cabinet, and the distribution box are disposed in a lower part of the base and are connected to the plurality of electrode assemblies; the conveying assembly is disposed in a middle part of the base; the base comprises an inlet for entry and an outlet for exit of a package to be sterilized; the shielding door is disposed next to the inlet and the outlet and configured to open and close the inlet and the outlet; the controller is disposed outside the housing, and comprises a control box and a touch control panel disposed on a front face of the control box; the control box comprises a programmable logic controller (PLC) connected to the touch control panel; the PLC is configured to control operations of the conveying assembly, the plurality of core modules, the transformer, the control cabinet, the distribution box, the shielding door, and the touch control panel; each of the plurality of electrode assemblies comprises an electrode pair and a transmission mechanism connected to the electrode pair; and the electrode pair comprises one or more groups of upper electrodes and lower electrodes oppositely disposed with respect to the upper electrodes; a distance between the upper electrode(s) and the lower electrode(s) is adjustable by the transmission mechanism; the lower electrode(s) is disposed below the conveying assembly and fixed on the housing, and the upper electrode(s) is movable with respect to the lower electrode(s) to press the package to be sterilized.

In a class of this embodiment, the plurality of core modules is 2-5 in number.

In a class of this embodiment, each of the plurality of core modules comprises 2-6 electrode assemblies.

In a class of this embodiment, the distance between centers of two adjacent core modules is 300-500 mm.

In a class of this embodiment, the conveying assembly comprises an active linear slide, a driven linear slide, a conveyor belt, a beam, and a servo motor; the active linear slide and the driven linear slide are vertically disposed oppositely to each other; two synchronous pulleys are respectively disposed on an inner side of the active linear slide and an inner side of the driven linear slide; the conveyor belt is movably wound on the two synchronous pulleys; the beam is movably disposed between the active linear slide and the driven linear slide; the servo motor is disposed on a lower end of the active linear slide to drive the beam to move up and down along with the active linear slide and the driven linear slide.

In a class of this embodiment, the upper electrode(s) comprises a high-voltage electrode, a fixed frame, a first insulating plate, a mounting plate, and a binding post; the first insulating plate is embedded in the fixed frame; the first insulating plate comprises an upper surface, and the upper surface comprises a first central depression; the high-voltage electrode is disposed in the first central depression; the mounting plate is disposed on the fixed frame and the first insulating plate; the mounting plate comprises a central through hole and the binding post is disposed in the through hole; the binding post comprises a first end extending to connect to the high-voltage electrode, and a second end extending through the beam; the first insulating plate comprises polymethylmethacrylate, phenolic resin or epoxy resin and has a dielectric constant of 3.5-5.0; and a thickness of the first insulating plate is 1.8-3.0 mm.

In a class of this embodiment, the distance between two ends of the upper electrode(s) and the transmission mechanism is no less than 150-180 mm.

In a class of this embodiment, the lower electrode(s) comprises a ground electrode, a base plate, and a second insulating plate; the base plate comprises an upper surface, and the upper surface comprises a second central depression; a grounding stud is disposed in the central depression; the ground electrode is disposed in the second central depression and is connected to the grounding stud; the second insulating plate is disposed on the ground electrode; the second insulating plate comprises polymethylmethacrylate, phenolic resin or epoxy resin and has a dielectric constant of 3.5-5.0; and a thickness of the second insulating plate is 3.0-4.5 mm.

In a class of this embodiment, the transformer comprises an output interface in parallel connection to the upper electrode(s) and the lower electrode(s) of the electrode assemblies via a high voltage shielding line; in the presence of a 220 V voltage, a 60-90 kV electric field is produced between the upper electrode(s) and the lower electrode(s).

In a class of this embodiment, the housing comprises a metal shell and an observation window, and the observation window comprises glass and a metal mesh shielding layer fastened to the glass.

In a class of this embodiment, the control box comprises an input and output port connected to a master computer of a production line.

In a class of this embodiment, the device further comprises an air blower, an alarm lamp, and a ground connector;

the air blower is disposed in the housing; the ground connector is disposed on the housing; the alarm lamp is disposed on the housing and connected to the PLC; when a fault occurs, the PLC controls the alarm lamp to send out a warning signal.

The following advantages are associated with the device cold plasma sterilization of the disclosure: in the presence of a 220 V voltage, a 60-90 kV electric field is produced between the upper electrode(s) and the lower electrode(s) of the device. The packed food is placed between the upper electrode(s) and the lower electrode(s). The high voltage electric filed stimulates the gas in the packed food to produce plasma thus achieving safe and efficient sterilization effect.

Figure 1:
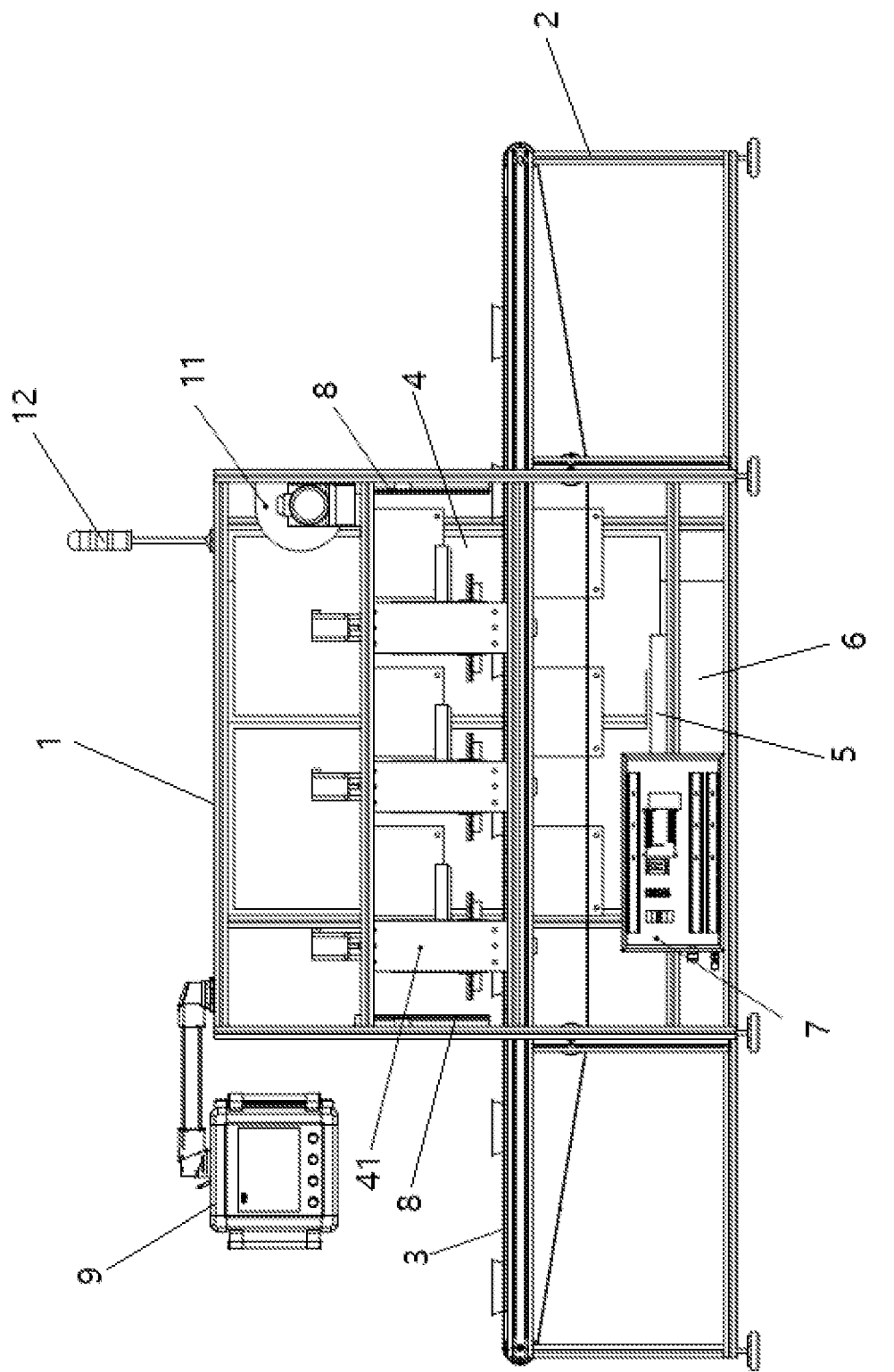
FIG. 1 is a schematic diagram of a device cold plasma sterilization in accordance with one embodiment of the disclosure.

In the drawings, the following reference numbers are used: 1. Housing; 2. Base; 3. Conveying assembly; 4. Core module; 5. High voltage transformer; 6. Control cabinet; 7. Distribution box; 8. Shielding door; 9. Controller; 10. Observation window; 11. Air blower; 12. Alarm lamp; 31. Motor; 32. Conveyor belt; 33. Transmission mechanism; 34. Drive roller; 35. Idler roller; 36. Tension roller; 41. Electrode assemblies; 42. Electrode pair; 43. Transmission mechanism; 91. Control box; 92. Touch control panel; 93. Input and output port; 421. Upper electrodes; 422. Lower electrodes; 431. Active linear slide; 432. Driven linear slide; 433. Conveyor belt; 434. Beam; and 435. Servo motor; 436. Synchronous pulleys; 4211. High-voltage electrode; 4212. Fixed frame; 4213. First insulating plate; 4214. Mounting plate; 4215. Binding post; 4216. First central depression; 4217. Guide post; 4221. Ground electrode; 4222. Base plate; 4223. Second insulating plate; 4224. Second central depression; and 4225. Grounding stud.

DETAILED DESCRIPTION

To further illustrate, embodiments detailing a device cold plasma sterilization are described below. It should be noted that the following embodiments are intended to describe and not to limit the disclosure.

Figure 2:
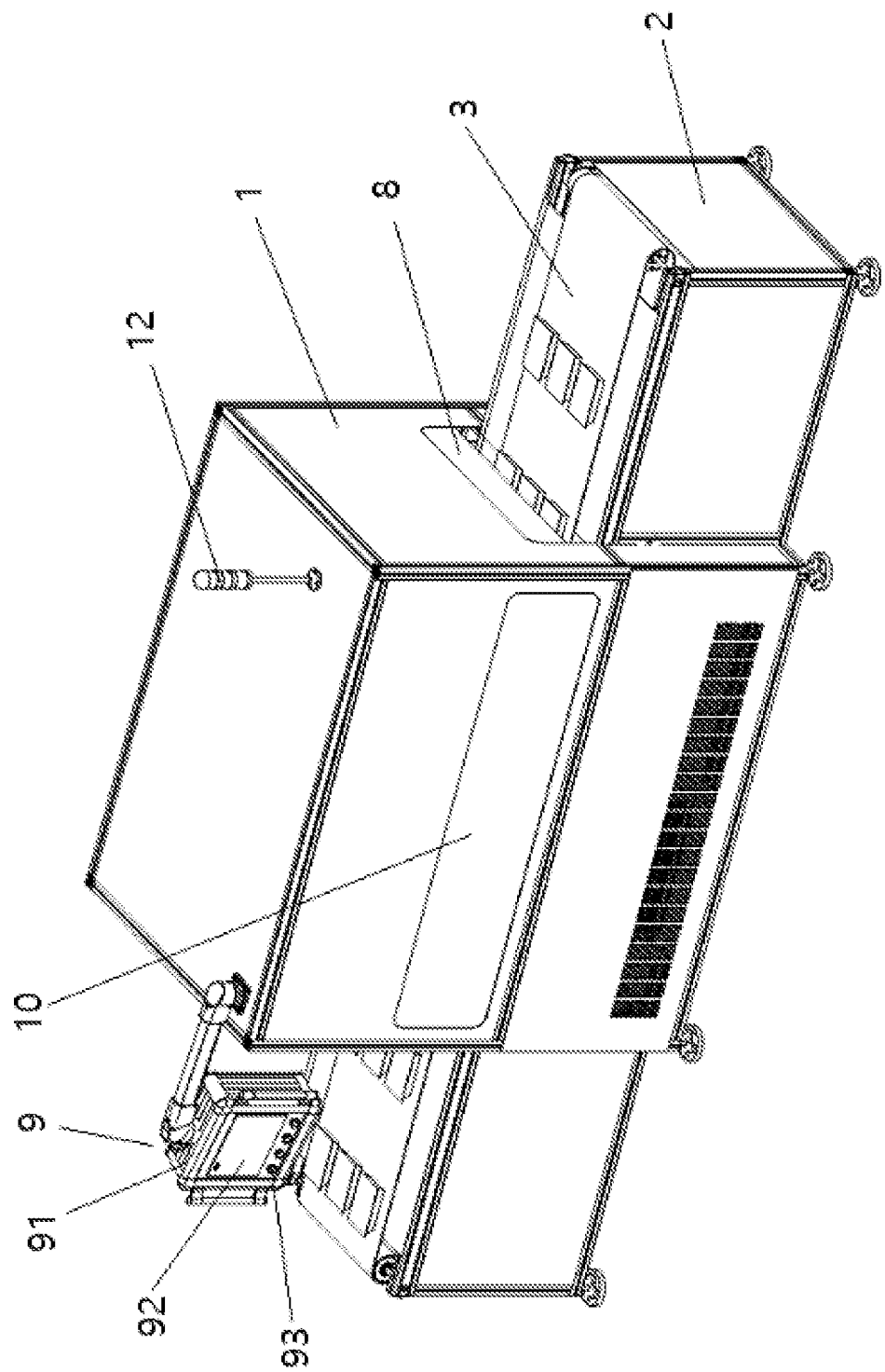
FIG. 2 is a three-dimensional diagram of a device cold plasma sterilization in FIG. 1.

As shown in FIGS. 1-2, provided is a device comprising a housing 1, a base 2, a conveying assembly 3, 2-5 core modules 4, a transformer 5, a control cabinet 6, a distribution box 7, a shielding door 8, and a controller 9. The housing 1 is disposed on the base 2. The 2-5 core modules 4 are disposed in the housing along a moving direction of the conveying assembly 3 and are spaced apart from each other. The 2-5 core modules 4 each comprise a plurality of electrode assemblies 41 spaced from one another by equal distance and arranged in a row. The transformer 5, the control cabinet 6, and the distribution box 7 are disposed in a lower part of the base 2 and are connected to the 2-6 electrode assemblies 41. The conveying assembly 3 is disposed in a middle part of the base 2. The base 2 comprises an inlet for entry and an outlet for exit of a package to be sterilized. The shielding door 8 is disposed next to the inlet and the outlet and configured to open and close the inlet and the outlet. The controller 9 is disposed outside the housing 1, and comprises a control box 91 and a touch control panel 92 disposed on a front face of the control box 91. The control box 91 comprises a programmable logic controller (PLC) connected to the touch control panel. The PLC is configured to control operations of the conveying assembly 3, the plurality of core modules 4, the transformer 5, the control cabinet 6, the distribution box 7, the shielding door 8, and the touch control panel 92.

A distance between centers of two adjacent core modules 4 is 300-500 mm.

In certain embodiments, the 2-5 core modules 4 each comprise a plurality of electrode assemblies 41 spaced from one another by equal distance and arranged in a row.

Figure 3:
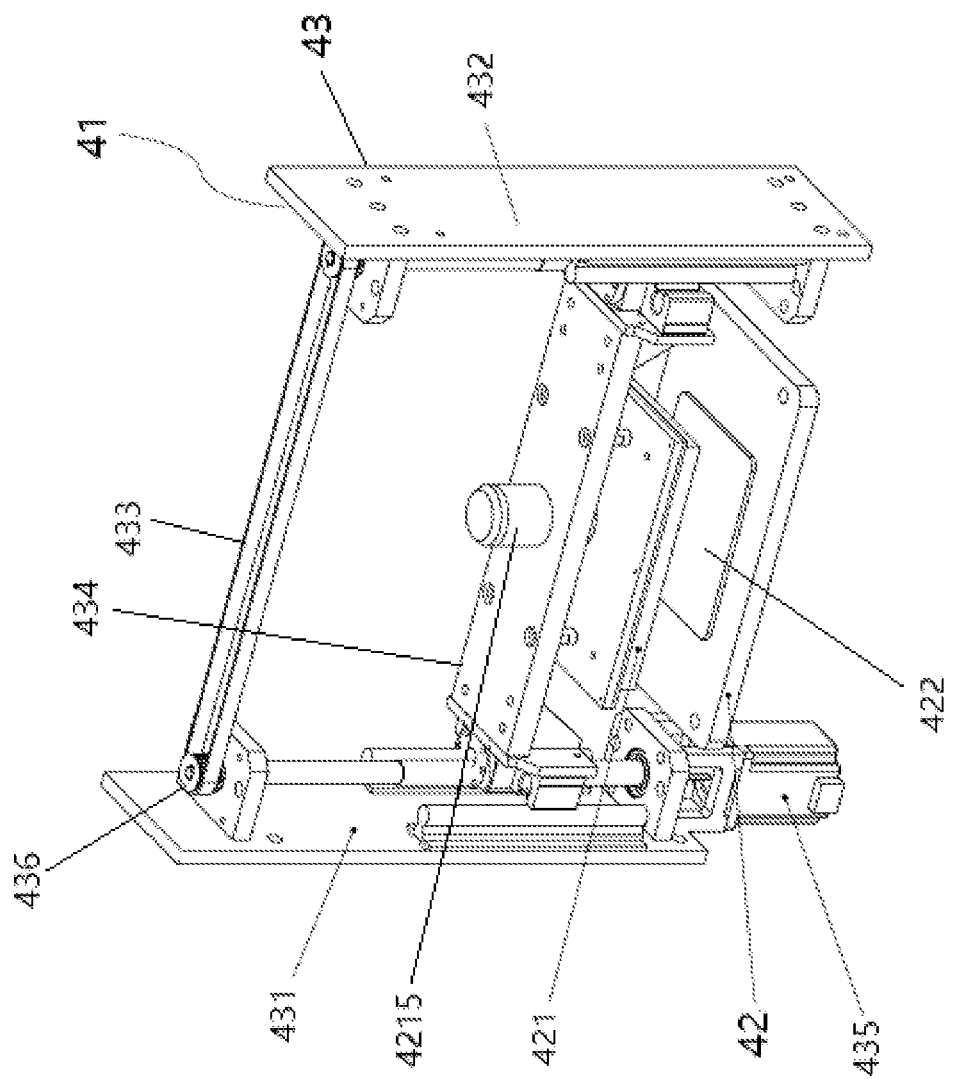
FIG. 3 is a schematic diagram of an electrode assembly of a device cold plasma sterilization in FIG. 1.

Referring to FIG. 3, the 2-6 electrode assemblies each comprise an electrode pair 42 and a transmission mechanism 43 connected to the electrode pair 42. The electrode pair 42 comprises one or more groups of upper electrodes 421 and lower electrodes 422 oppositely disposed with respect to the upper electrodes. A distance between the upper electrode(s) 421 and the lower electrode(s) 422 is adjustable by the transmission mechanism 43. The lower electrode(s) 422 is disposed below the conveying assembly 3 and fixed on the housing 2, and the upper electrode(s) 421 is movable with respect to the lower electrode(s) 422 to press the package to be sterilized.

The conveying assembly 3 comprises an active linear slide 431, a driven linear slide 432, a conveyor belt 433, a beam 434, and a servo motor 435. The active linear slide 431 and the driven linear slide 432 are vertically disposed oppositely to each other. Two synchronous pulleys 436 are respectively disposed on an inner side of the active linear slide 431 and an inner side of the driven linear slide 432. The conveyor belt 433 is movably wound on the two synchronous pulleys 436. The beam 434 is movably disposed between the active linear slide 431 and the driven linear slide 432. The servo motor 435 is disposed on a lower end of the active linear slide 431 to drive the beam 434 to move up and down along with the active linear slide 431 and the driven linear slide 432.

In certain embodiments, the electrode pair 42 comprises one or more groups of upper electrodes 421 and lower electrodes 422 oppositely disposed with respect to the upper electrodes. The length of the conveyor belt 433 increases with the increase of the distance between the active linear slide 431 and the driven linear slide 432 (If the distance is too large, the beam 434 may get tilted owing to the movement of the conveyor belt 433. In this case, an electric sliding table equipped with a double servo motor may be used in combination with the PLC to achieve synchronized operation).

Figure 4:
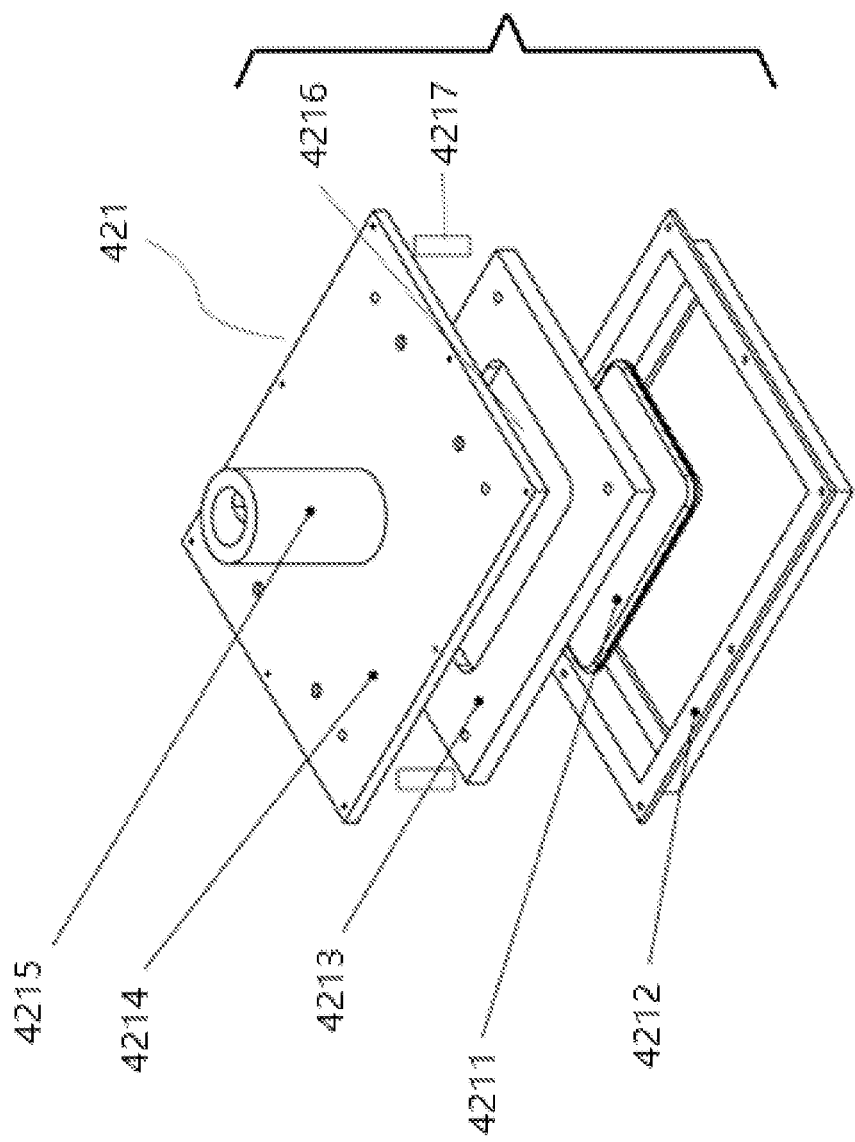
FIG. 4 is an exploded view of an upper electrode of a device cold plasma sterilization in FIG. 3.

Referring to FIG. 4, the upper electrode(s) 421 comprises a high-voltage electrode 4211, a fixed frame 4212, a first insulating plate 4213, a mounting plate 4214, and a binding post 4215. The first insulating plate 4213 is embedded in the fixed frame 4212. The first insulating plate 4213 comprises an upper surface, and the upper surface comprises a first central depression 4216.

The high-voltage electrode 4211 is disposed in the first central depression 4216; the mounting plate 4214 is disposed on the fixed frame 4212 and the first insulating plate 4213; the mounting plate 4214 comprises a central through hole and the binding post 4215 is disposed in the through hole. The binding post 4215 comprises a first end extending to connect to the high-voltage electrode 4211, and a second end extending through the beam 434. The movement of the beam 434 leads to the movement of the binding post 4215, and so does the upper electrodes 421. The first insulating plate 4213 comprises polymethylmethacrylate, phenolic resin or epoxy resin and has a dielectric constant of 3.5-5.0; and the thickness of the first insulating plate 4213 is 1.8-3.0 mm. In certain embodiments, the high-voltage electrode 4211, the fixed frame 4212, the first insulating plate 4213, and the mounting plate 4214 are in sealed connection.

The first insulating plate 4213 is connected to the mounting plate 4214 via a guide post 4217. A spring (no shown) is disposed around the guide post 4217. The spring and the guide post constitute an entire structure. When the high-voltage electrode 4211 contacts the package to be sterilized, the entire structure is slightly pressed and the package is compacted by the high-voltage electrode 4211. The high-voltage electrode 4211 discharge electrons with a dielectric barrier discharge method.

Figure 5:
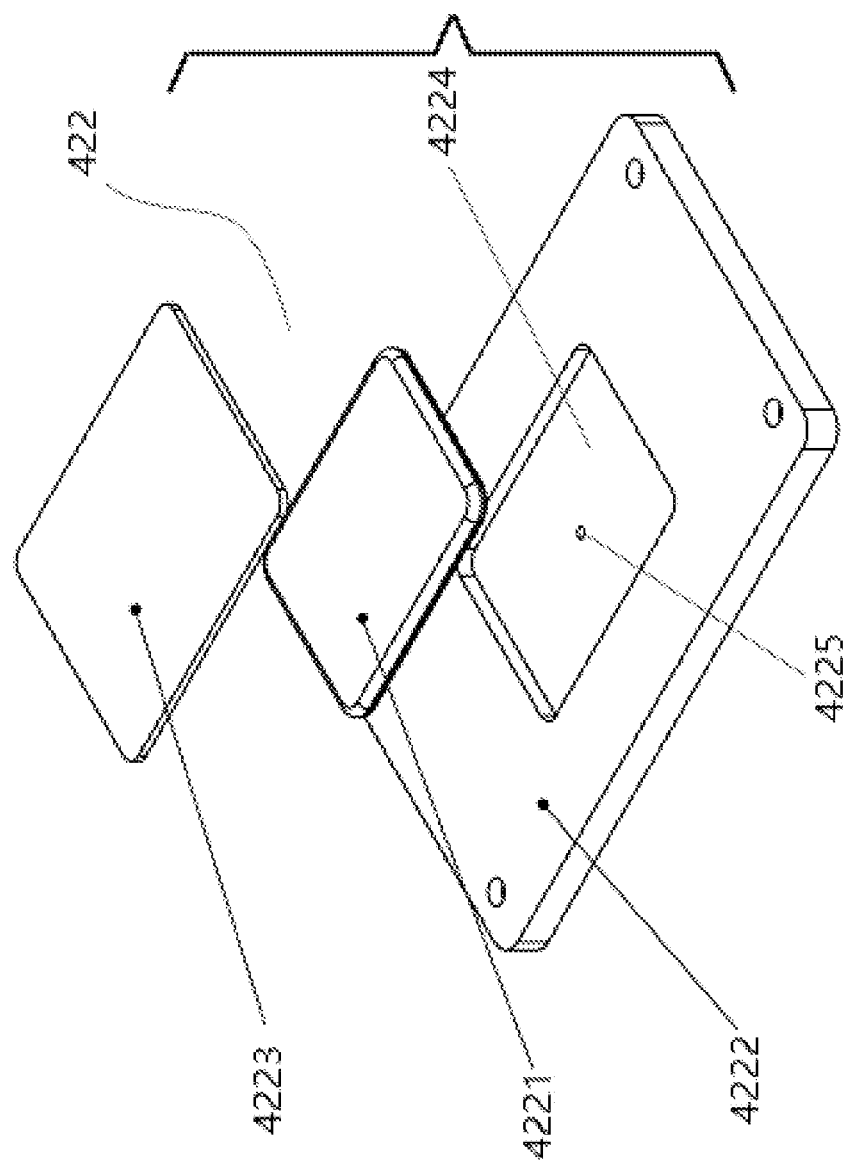
FIG. 5 is an exploded view of a lower electrode of a device cold plasma sterilization in FIG. 3.

Referring to FIG. 5, the lower electrode(s) 422 comprises a ground electrode 4221, a base plate 4222, and a second insulating plate 4223. The base plate 4222 comprises an upper surface, and the upper surface comprises a second central depression 4224. A grounding stud 4225 is disposed in the central depression 4224. The ground electrode 4221 is disposed in the second central depression 4224 and is connected to the grounding stud 4225. The second insulating plate 4223 is disposed on the ground electrode 4221. The second insulating plate 4223 comprises polymethylmethacrylate, phenolic resin or epoxy resin and has a dielectric constant of 3.5-5.0. The thickness of the second insulating plate 4223 is 3.0-4.5 mm.

The structural units of the upper electrode(s) 421 and the lower electrode(s) 422 are mutually sealed thus preventing the creepage between the upper electrode(s) 421 and the lower electrode(s) 422 under high voltage. The high-voltage electrode 4211 and the ground electrode 4221 both comprise aluminum because of its light weight and durability.

In certain embodiments, a distance between two ends of the upper electrode(s) 421 and the transmission mechanism 43 is no less than 150-180 mm. The active linear slide 431 and the driven linear slide 432 both comprise metals. When the distance between the upper electrode(s) 421 and/or the lower electrode(s) 422 and the linear slide 431 and/or the driven linear slide 432 is too close, a current may be generated, posing hidden risks. In certain embodiments, an optimal distance can be obtained through a number of experiments. The optimal distance ensures that the upper electrode(s) 421 and the lower electrode(s) 422 operates under normal condition, almost unaffected by the linear slide 431 and the driven linear slide 432.

EXAMPLE

Sterilization of instant betel nut with the first insulating plate having different dielectric constants.

Experimental Method

The instant betel nut was inoculated with a micro-organism and incubated to allow the micro-organism to grow (400,000 colonies total). 10 g of the inoculated instant betel nut was packed into a packaging bag, and cold sterilized using the first insulating plate having different dielectric constants.

Sterilization Condition

Cold sterilization for 30 s with a 90 s interval for three cycles, at a voltage intensity of 16.5 kV/cm, a current of 0.9 mA, an operating room temperature of 25° C., and a humidity of 55%.

Bactericidal Effect

Total number (CFU/g) of colonies on the sterilized instant betel nut is shown in Table 1:

TABLE 1

| Material | Poly-ethylene | Poly-propylene | Epoxy resin | Polymethyl-methacrylate | Phenolic Resin |
|---|---|---|---|---|---|
| Dielectric constant | 2.3 | 2.3 | 3.5 | 3.7 | 4.8 |
| Total number of colonies after sterilization | 46000 | 46000 | 22000 | 20000 | 18000 |
| Rate of microbial death | 88.5% | 88.5% | 94.5% | 95% | 95.5% |

The transformer 5 comprises an output interface in parallel connection to the upper electrode(s) 421 and the lower electrode(s) 422 of the electrode assemblies 41 via a high voltage shielding line. In the presence of a 220 V voltage, a 60-90 kV electric field is produced between the upper electrode(s) 421 and the lower electrode(s) 422.

The upper electrode(s) 421 and the lower electrode(s) 422 are both high-voltage electrodes and connected respectively to the transformer 5. The upper electrode(s) 421 is disposed on the transmission mechanism 43, and moves up and down along with the active linear slide 431 and the driven linear slide 432. The lower electrode(s) 422 is disposed below the conveying assembly 3. A high-voltage electric field is formed in the space above the conveyor belt and ionizes the air inside the package, thereby transferring electron and generating plasma. The plasma is used for the microorganism surface sterilization of foods using. Each production line may comprise one or more electrode assemblies 41 in accordance with different technical requirements. In certain embodiments, three electrode assemblies 41 are used for detailing the disclosure.

Figure 6:
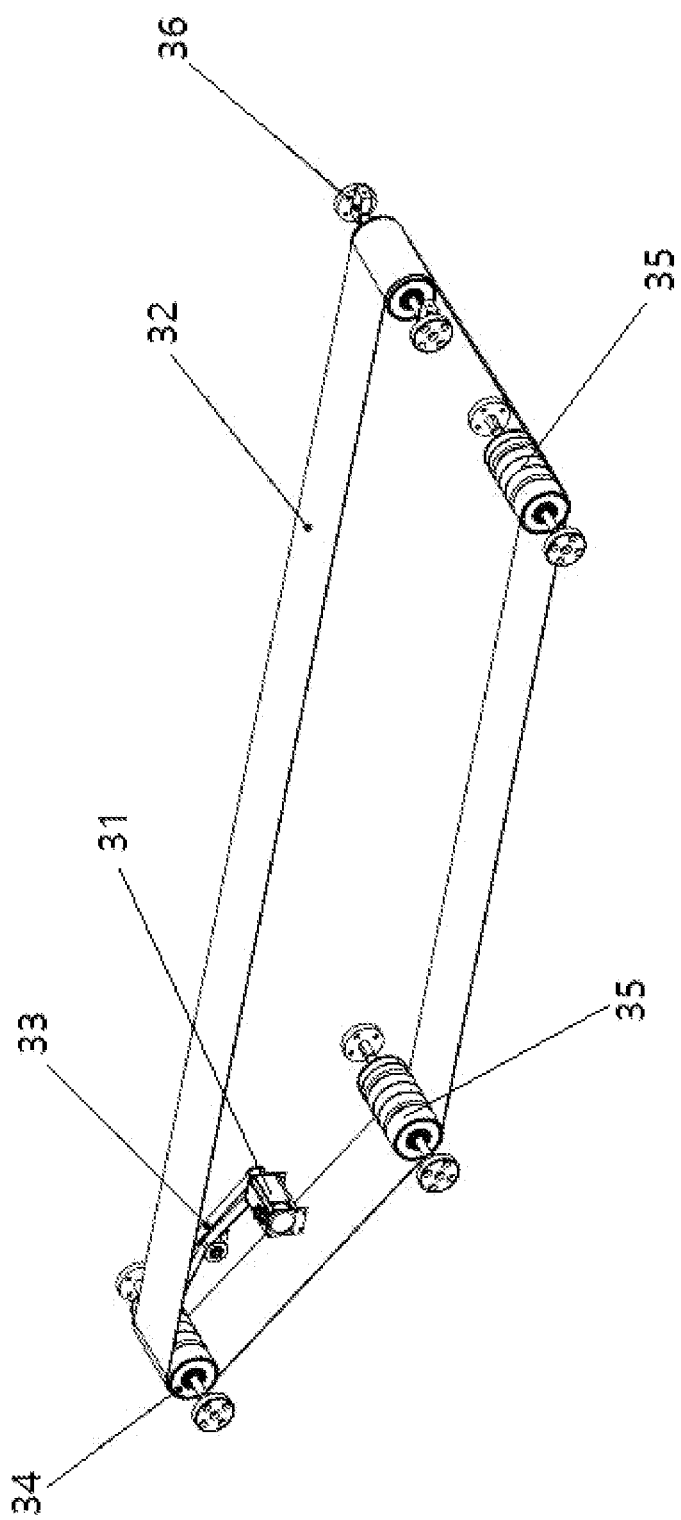
FIG. 6 is a schematic diagram of a conveying assembly of a device cold plasma sterilization in FIG. 1.

Referring to FIG. 6, the conveying assembly 3 comprises a motor 31, a conveyor belt 32, a transmission mechanism 33, a drive roller 34, and at least two driven rollers 35, and a tension roller 36. The conveying assembly 3 is configured to support and transport the materials to be sterilized.

The drive roller 34 and the tension roller 36 are disposed respectively on both sides of the base 2. The at least two driven rollers 35 are disposed respectively beneath the drive roller 34 and the tension roller 36. The conveyor belt 32 is wound around the drive roller 34, the at least two driven rollers 35, and the tension roller 36, thereby giving the conveying assembly 3 an inverted trapezoid structure. The motor 31 is connected to the drive roller 34 via the transmission mechanism 33. The conveyor belt 32 comprises nylon or rubber without any metallic materials.

In certain embodiments, the motor 31 is a servo motor that can accurately control the movement and stop of the conveyor belt. The conveyor belt 32 comprises silica gel thus ensuring the mechanical strength for the transport of workpieces, and in the process of discharge, the conveyor belt functions as a dielectric barrier plate of the lower electrode 422. The length of the production line determines the number and position of the driven rollers 35 and the tension roller 36. In certain embodiments, the drive roller 34 is disposed in the opposite direction of the tension roller 36. The two driven rollers 35 are disposed beneath the drive roller 34 and the tension roller 36. A connection device (not shown) and a metronome (not shown) are disposed respectively on both sides of the conveying assembly 3 to provide accurate positioning for the materials being transported along the belt.

Referring to FIG. 2, the housing 1 comprises a metal shell and an observation window 10 disposed on the obverse side of the production line. The observation window 10 comprises glass and a metal mesh shielding layer fastened to the glass. The conveyor belt 32 further comprises a vertical-lift shielded door 8 for the housing 1. The shielded door 8 is lowered to block the high-voltage electrical field when an electrical discharge takes place. The shielded door 8 comprises an aluminum alloy plate.

The controller 9 comprises a control box 91 and a touch control panel 92, and can work independently or be controlled by a master computer. The control box 91 comprises a programmable logic controller (PLC) which is configured to receive all the detection signals from the device and send out all the control signals to the device. The control box 91 further comprises an input and output port 93 connected to a master computer of a production line, which allows the device to be controlled by the touch control panel 92 or the master computer that provides automation in production.

In certain embodiments, the device further comprises an air blower 11, an alarm lamp 12, and a ground connector. The air blower 11 is disposed in the housing 1. The ground connector is disposed on the housing. The alarm lamp 12 is disposed on the housing 1 and connected to the PLC. When a fault occurs, the PLC controls the alarm lamp to send out a warning signal.

Safety protection for the device cold plasma sterilization of the disclosure:
1. Protection against high-voltage breakdown. Overcurrent protection is used in the host power supply of a differential power supply. When the current level gets too high, the power is cut off to prevent electrical breakdown due to high voltage.
2. Protection for high-voltage insulation. Insulating materials are used to separate electrically the conducting parts such as high-voltage cables, terminals, electrode plates, etc. Each of the conducting parts has a distance through insulation of 150-180 mm.
3. Protection for high-voltage electric field. The device is shielded by a metal housing. The metal mesh shielding layer is fastened to the observation window. The conveyor belt comprises a vertical-lift shielded door for the housing. The shielded door is closed to block the high-voltage electrical field when an electrical discharge takes place.
4. Power-off protection when opening the door. All the doors that can be opened comprise respectively a proximity sensor. When the device is not being debugged, the device cannot work unless all the doors are closed.

It will be obvious to those skilled in the art that changes and modifications may be made, and therefore, the aim in the appended claims is to cover all such changes and modifications.

What is claimed is:
1. A device, comprising:
a housing;
a base;
a conveying assembly;
a plurality of core modules;
a transformer;
a control cabinet;
a distribution box;
a shielding door; and
a controller;
wherein:
the housing is disposed on the base;
the plurality of core modules is disposed in the housing along a moving direction of the conveying assembly and are spaced apart from each other;
each of the plurality of core modules comprises a plurality of electrode assemblies spaced from one another by equal distance and arranged in a row;
the transformer, the control cabinet, and the distribution box are disposed in a lower part of the base and are connected to the plurality of electrode assemblies;
the conveying assembly is disposed in a middle part of the base;
the base comprises an inlet for entry and an outlet for exit of a package to be sterilized;
the shielding door is disposed next to the inlet and the outlet and configured to open and close the inlet and the outlet;
the controller is disposed outside the housing, and comprises a control box and a touch control panel disposed on a front face of the control box;
the control box comprises a programmable logic controller (PLC) connected to the touch control panel; the PLC is configured to control operations of the conveying assembly, the plurality of core modules, the transformer, the control cabinet, the distribution box, the shielding door, and the touch control panel;
each of the plurality of electrode assemblies comprises an electrode pair and a transmission mechanism connected to the electrode pair; and
the electrode pair comprises one or more groups of upper electrodes and lower electrodes oppositely disposed with respect to the upper electrodes; a distance between the upper electrode(s) and the lower electrode(s) is adjustable by the transmission mechanism; the lower electrode(s) is disposed below the conveying assembly and fixed on the housing, and the upper electrode(s) is movable with respect to the lower electrode(s) to press the package to be sterilized.

2. The device of claim 1, wherein the plurality of core modules is 2-5 in number.

3. The device of claim 1, wherein each of the plurality of core modules comprises 2-6 electrode assemblies.

4. The device of claim 1, wherein a distance between centers of two adjacent core modules is 300-500 mm.

5. The device of claim 1, wherein the conveying assembly comprises an active linear slide, a driven linear slide, a conveyor belt, a beam, and a servo motor; the active linear slide and the driven linear slide are vertically disposed oppositely to each other; two synchronous pulleys are respectively disposed on an inner side of the active linear slide and an inner side of the driven linear slide; the conveyor belt is movably wound on the two synchronous pulleys; the beam is movably disposed between the active linear slide and the driven linear slide; the servo motor is disposed on a lower end of the active linear slide to drive the beam to move up and down along with the active linear slide and the driven linear slide.

6. The device of claim 5, wherein the upper electrode(s) comprises a high-voltage electrode, a fixed frame, a first insulating plate, a mounting plate, and a binding post; the first insulating plate is embedded in the fixed frame; the first insulating plate comprises an upper surface, and the upper surface comprises a first central depression; the high-voltage electrode is disposed in the first central depression; the mounting plate is disposed on the fixed frame and the first insulating plate; the mounting plate comprises a central through hole and the binding post is disposed in the through hole; the binding post comprises a first end extending to connect to the high-voltage electrode, and a second end extending through the beam; the first insulating plate comprises polymethylmethacrylate, phenolic resin or epoxy resin and has a dielectric constant of 3.5-5.0; and a thickness of the first insulating plate is 1.8-3.0 mm.

7. The device of claim 6, wherein a distance between two ends of the upper electrode(s) and the transmission mechanism is no less than 150-180 mm.

8. The device of claim 1, wherein the lower electrode(s) comprises a ground electrode, a base plate, and a second insulating plate; the base plate comprises an upper surface, and the upper surface comprises a second central depression; a grounding stud is disposed in the central depression; the ground electrode is disposed in the second central depression and is connected to the grounding stud; the second insulating plate is disposed on the ground electrode; the second insulating plate comprises polymethylmethacrylate, phenolic resin or epoxy resin and has a dielectric constant of 3.5-5.0; and a thickness of the second insulating plate is 3.0-4.5 mm.

9. The device of claim 1, wherein the transformer comprises an output interface in parallel connection to the upper electrode(s) and the lower electrode(s) of the electrode assemblies via a high voltage shielding line; in the presence of a 220 V voltage, a 60-90 kV electric field is produced between the upper electrode(s) and the lower electrode(s).

10. The device of claim 1, wherein the housing comprises a metal shell and an observation window, and the observation window comprises glass and a metal mesh shielding layer fastened to the glass.

11. The device of claim 1, wherein the control box comprises an input and output port connected to a master computer of a production line.

12. The device of claim 1, further comprising an air blower, an alarm lamp, and a ground connector, wherein the air blower is disposed in the housing; the ground connector is disposed on the housing; the alarm lamp is disposed on the housing and connected to the PLC; when a fault occurs, the PLC controls the alarm lamp to send out a warning signal.

* * * * *